(12) United States Patent
Sheetz

(10) Patent No.: US 9,295,809 B2
(45) Date of Patent: Mar. 29, 2016

(54) FIXATION AND PROTECTION OF AN IMPLANTED MEDICAL DEVICE

(75) Inventor: Kevin W. Sheetz, Sandy, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 1012 days.

(21) Appl. No.: 13/428,913

(22) Filed: Mar. 23, 2012

(65) Prior Publication Data

US 2013/0072901 A1    Mar. 21, 2013

Related U.S. Application Data

(60) Provisional application No. 61/467,330, filed on Mar. 24, 2011.

(51) Int. Cl.
*A61M 25/00* (2006.01)
*A61M 39/02* (2006.01)

(52) U.S. Cl.
CPC ....... *A61M 25/0043* (2013.01); *A61M 25/0054* (2013.01); *A61M 39/0247* (2013.01); *A61M 2025/0056* (2013.01); *A61M 2025/0059* (2013.01); *A61M 2039/0261* (2013.01)

(58) Field of Classification Search
CPC ..................... A61M 25/0043; A61M 39/0247; A61M 25/0054; A61M 2025/0056; A61M 2039/0261; A61M 2025/0059
USPC ........................................ 604/508, 175, 8–10
See application file for complete search history.

(56) References Cited

U.S. PATENT DOCUMENTS

| 4,934,226 | A | | 6/1990 | Dacey, Jr. |
| 5,217,493 | A | | 6/1993 | Raad et al. |
| 5,316,348 | A | * | 5/1994 | Franklin .......................... 285/39 |
| 5,389,091 | A | * | 2/1995 | Moorehead .................... 604/524 |
| 5,624,704 | A | | 4/1997 | Darouiche et al. |
| 5,800,450 | A | | 9/1998 | Lary et al. |
| 5,902,283 | A | | 5/1999 | Darouiche et al. |
| 5,906,596 | A | | 5/1999 | Tallarida |
| 5,984,857 | A | * | 11/1999 | Buck et al. ....................... 600/16 |
| 6,120,491 | A | | 9/2000 | Kohn et al. |

(Continued)

FOREIGN PATENT DOCUMENTS

| EP | 0022370 A1 | 1/1981 |
| EP | 0194980 A2 | 9/1986 |

(Continued)

OTHER PUBLICATIONS

WO 2009085281, Kupparathanam, date: 2009.*

(Continued)

*Primary Examiner* — Manuel Mendez
(74) *Attorney, Agent, or Firm* — Rutan & Tucker, LLP

(57) ABSTRACT

Fixation and protective components for use with implantable medical devices, such as access ports and catheters, are disclosed. In one embodiment, a protective sleeve is employed about a catheter so as to distribute compressive loads and ensure patency of the catheter lumen, even in areas prone to pinch-off. A catheter assembly in one embodiment thus comprises an elongate catheter tube that defines at least one lumen. A protective mesh sleeve is disposed about an external portion of the catheter tube so as to cover at least a portion of the longitudinal length of the catheter tube. The protective sleeve is configured to distribute a compressive load on the catheter tube so as to ensure patency of the at least one lumen of the catheter tube.

9 Claims, 9 Drawing Sheets

(56) References Cited

U.S. PATENT DOCUMENTS

| | | |
|---|---|---|
| RE37,160 E | 5/2001 | Kohn et al. |
| 6,427,089 B1 | 7/2002 | Knowlton |
| D501,539 S * | 2/2005 | Dyer, III .................. D23/262 |
| 7,766,880 B1 | 8/2010 | Spinoza |
| 7,905,874 B2 | 3/2011 | Miller et al. |
| 8,315,700 B2 | 11/2012 | Citron et al. |
| 8,591,531 B2 | 11/2013 | Buevich et al. |
| 2006/0173424 A1 | 8/2006 | Conlon |
| 2006/0200111 A1 | 9/2006 | Moehle et al. |
| 2007/0198040 A1 | 8/2007 | Buevich et al. |
| 2008/0128315 A1 | 6/2008 | Buevich et al. |
| 2008/0132922 A1 | 6/2008 | Buevich et al. |
| 2008/0241212 A1 | 10/2008 | Moses et al. |
| 2008/0262406 A1 * | 10/2008 | Wiener ................. 604/8 |
| 2009/0018559 A1 | 1/2009 | Buevich et al. |
| 2009/0088548 A1 | 4/2009 | Moses et al. |
| 2009/0198197 A1 * | 8/2009 | Bischoff et al. .............. 604/265 |
| 2010/0015237 A1 | 1/2010 | Moses et al. |
| 2010/0130478 A1 | 5/2010 | Moses et al. |
| 2011/0294760 A1 | 12/2011 | Bahulekar et al. |
| 2012/0052292 A1 | 3/2012 | Pulapura et al. |

FOREIGN PATENT DOCUMENTS

| | | |
|---|---|---|
| WO | 9818506 A1 | 5/1998 |
| WO | 2009085281 A1 | 7/2009 |
| WO | 2012129516 A1 | 9/2012 |

OTHER PUBLICATIONS

Louis, P., "Resorbable mesh as a containment system in reconstruction of the atrophic mandible fracture" J Oral Maxillofac Surg. Jun. 2004;62(6):719-23 (Abstract).

PCT/US12/30394 filed Mar. 23, 2012 International Preliminary Report on Patentability dated Oct. 3, 2013.

PCT/US12/30394 filed Mar. 23, 2012 International Search Report dated Aug. 17, 2012.

PCT/US12/30394 filed Mar. 23, 2012 Written Opinion dated Aug. 17, 2012.

Tyrx Website, "Our Technology: Bioresorbable Polymers," accessible at <<http://www.tyrx.com/technology-our-tech-overview.htm>>, last accessed Jul. 23, 2014.

Tyrx Website, AIGISRx Overview, accessible at <<http://www.tyrx.com/AIGISRx-Clinicians.htm>>, last accessed Jul. 23, 2014.

EP 12760194.6 filed Aug. 28, 2013 Extended European Search Report dated Aug. 7, 2014.

* cited by examiner

FIXATION AND PROTECTION OF AN IMPLANTED MEDICAL DEVICE

CROSS-REFERENCE TO RELATED APPLICATIONS

This application claims the benefit of U.S. Provisional Patent Application No. 61/467,330, filed Mar. 24, 2011, and titled "Antimicrobial Fixation Device for an Implantable Medical Device," which is incorporated herein by reference in its entirety.

BRIEF SUMMARY

Briefly summarized, embodiments of the present invention are directed to fixation and protective components for use with implantable medical devices, such as access ports and catheters. In one embodiment, configurations for directly securing an implantable medical device within a tissue pocket of the patient are disclosed. In another embodiment, indirect securement of the medical device within the pocket using a fixation component is disclosed. In yet another embodiment, a protective sleeve is employed about a catheter so as to ensure patency of the catheter lumen, even in areas prone to excess catheter tube compression and pinch-off.

For example, a catheter assembly in one embodiment comprises an elongate catheter tube that defines at least one lumen. A protective mesh sleeve is disposed about an external portion of the catheter tube so as to cover at least a portion of the longitudinal length of the catheter tube. The protective sleeve is configured to distribute a compressive load on the catheter tube so as to ensure patency of the at least one lumen of the catheter tube, thus enabling fluids to acceptably flow through the catheter tube.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to fixation and protective components for use with implantable medical devices, such as access ports and catheters. In one embodiment, configurations for directly securing an implantable medical device within a tissue pocket of the patient are disclosed. In another embodiment, indirect securement of the medical device within the pocket using a fixation component is disclosed. In yet another embodiment, a protective sleeve is employed about a catheter so as to ensure patency of the catheter lumen, even in areas prone to pinch-off.

Figure 1:
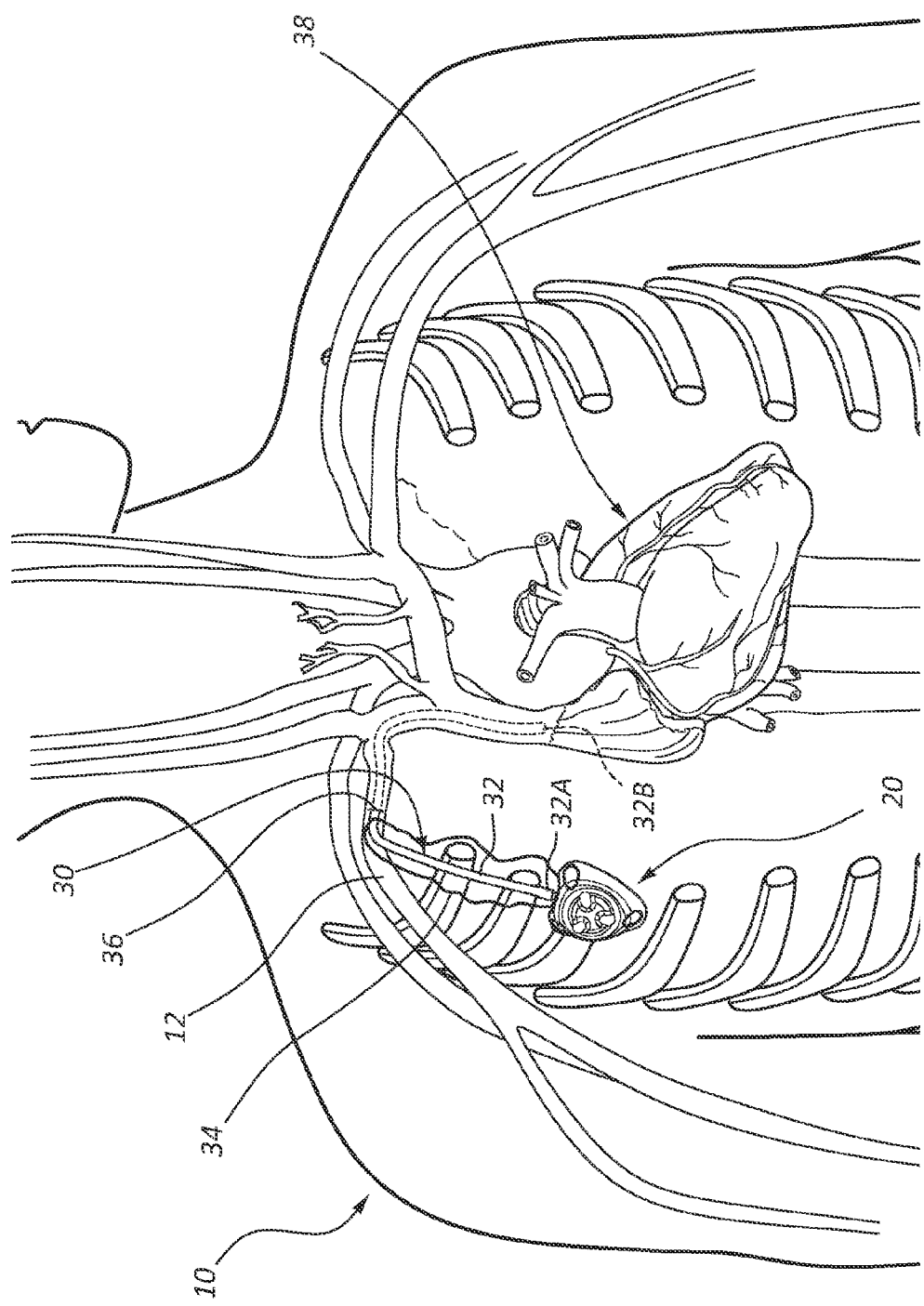
FIG. 1 is a simplified view showing placement of an implantable access port and catheter into a body of a patient.

Reference is first made to FIG. 1, which shows in simplified form internal portions of a patient body 10, including a subclavian vein 12, which is representative of veins into which a catheter may be inserted for the delivery of medicaments to the patient, for instance. An implantable access port ("port") 20 is shown after placement into the body 10 and is operably connected to a catheter 30. Specifically, the catheter 30 includes a catheter tube 32 defining a proximal end 32A that operably attaches to a stem of the port 20. A distal portion of the catheter tube 32 is disposed within the subclavian vein 12 such that a distal end 32B of the catheter tube is disposed proximate the heart 38 of the patient. Note that the catheter can be disposed in any one of a variety of vessels or other internal portions of the body 10, in addition to what is shown here.

In greater detail, both the port 20 and the catheter 30 are disposed beneath the patient's skin after placement by a health professional. The port 20 is typically disposed within a subcutaneous pocket defined within the tissue of the patient. Note that the particular placement of the port shown in FIG. 1 is merely one example of possible port placement. A tunneled portion 34 of the catheter tube 32 extends through the subcutaneous tissue of the patient from port pocket at the proximal catheter tube end 32A to a vessel insertion site 36, where the catheter tube enters the vein 12. As mentioned, the distal portion of the catheter tube 32 extends within the vein 12 toward the heart, as shown, and terminates at the distal catheter tube end 32B.

Figure 2:
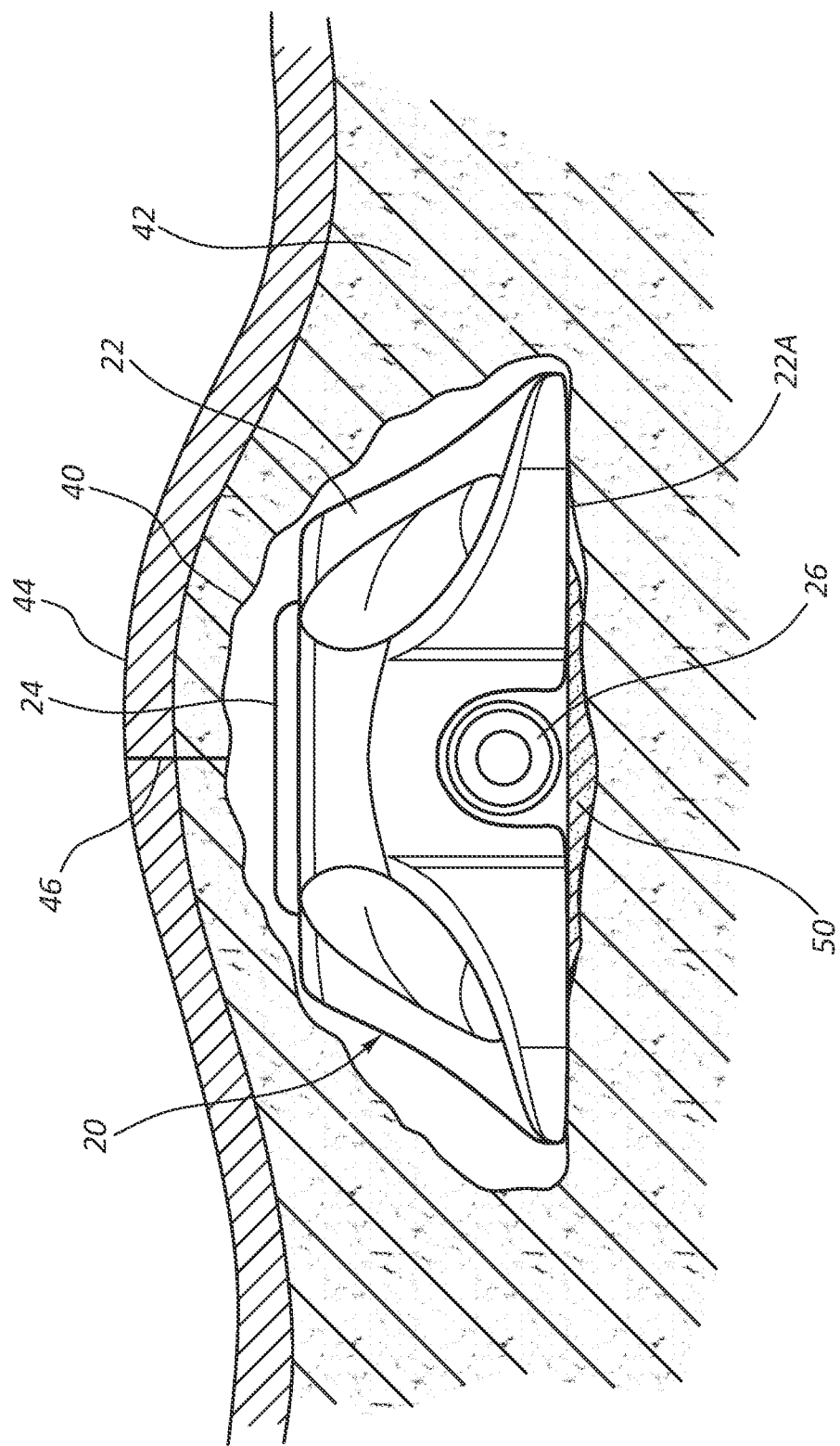
FIG. 2 shows an implantable access port secured within a tissue pocket according to one embodiment.

FIG. 2 shows the port 20 disposed in a tissue pocket 40 defined in tissue 42 below the skin 44 of the patient, as mentioned above. An incision 46 is also shown, used to access the pocket 40 and place the port 20 therein. As shown, the port 20 generally includes a body 22 to which is attached a needle-penetrable septum 24 that covers a fluid reservoir. A stem 26 extends from the body and is configured to be received by the proximal end 32A of the catheter tube 32 so as to establish fluid communication between the fluid reservoir and the lumen of the catheter 30.

In accordance with one embodiment, the port 20 is secured directly to the tissue pocket 40 via use of an adhesive 50 interposed between a bottom surface 22A of the port and a surface of the pocket. Thus adhesive 50 thus prevents undesired movement of the port 20 within the pocket 40. In one embodiment, therefore, the tissue pocket 40 is first created by the health care professional. The adhesive 50 is then applied to the bottom (or other suitable) surface 22A of the port 20, the pocket surface, or to both surfaces. The port 20 is then placed into the pocket 40 and pressed into place, if needed. In one embodiment, the port 20 is manually or otherwise temporarily secured until the adhesive cures. The stem 26 of the port 20 is attached to the proximal end 32A of the catheter 30 if the catheter has been previously inserted into the vein 12 (FIG. 1) and subcutaneously tunneled to the pocket 40. The pocket 40 is then subsequently closed at the incision 46.

The adhesive 50 can include any biocompatible substance that is sufficient for securing the port 20 in place. Examples of suitable adhesives include wound closure adhesives, a silicone-based MG 7-9850 AB adhesive available from Dow Corning, butyl-Z-cyanoacrylate, 2-Octyl-cyanoacrylate, and DERMABOND™ adhesive available from Ethicon, Inc. Of course, other suitable substances may also be used. In another embodiment, the adhesive may be absorbable/resorbable, or may include biocompatible epoxy, light-cured, heat-cured, or time-cured adhesives.

Figure 3A:
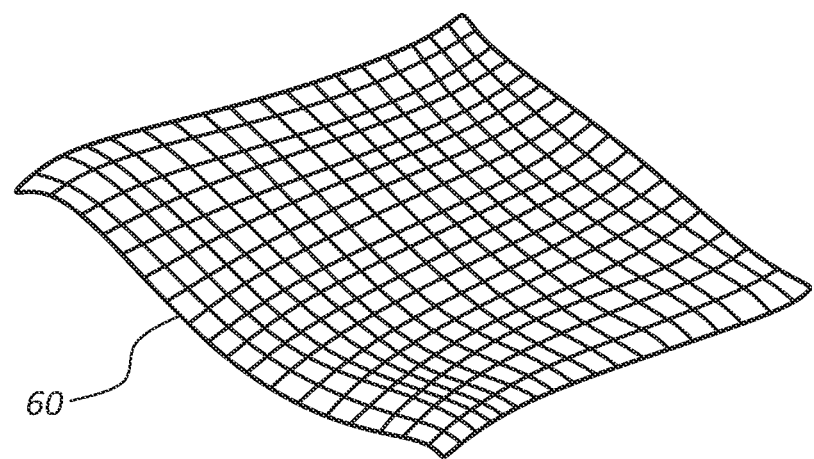
FIG. 3A is a perspective view of a mesh-based fixation component for an implantable medical device according to one embodiment.
Figure 3B:
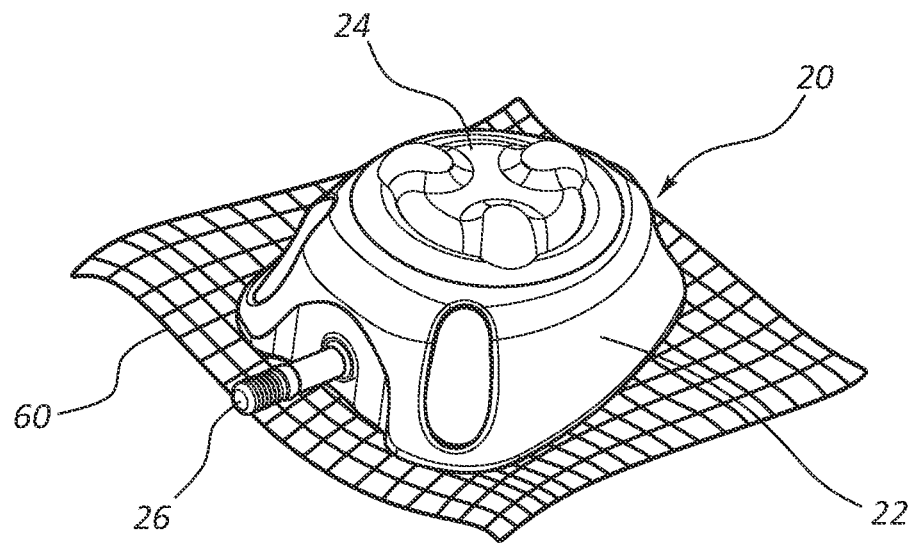
FIG. 3B is a perspective view of the fixation component of FIG. 3A attached to an implantable access port according to one embodiment.

FIGS. 3A and 3B depict various details of a fixation component for securing a port or other medical device within a tissue pocket, according to one embodiment. In particular, the fixation component of the present embodiment includes a flexible mesh sheet 60 of woven or intersecting strand material design. In one embodiment, synthetic materials including polypropylene, para-aramid synthetic fiber sold under the trademark KEVLAR®, polyethylene fibers sold under the trademark TYVEK®, polyamides such as nylon, semi-synthetic materials such as rayon, etc.

The size and shape of the holes defined by the mesh, as well as the size and material type of the strands can vary, but in one embodiment the mesh size is selected so as to promote tissue in-growth into the mesh. As such, the representation of the mesh sheet shown and described here is merely one example and is not meant to be limiting. In one embodiment, the strand diameter is about 0.005 inch or less to provide flexibility to the sheet. In one embodiment, the size of the mesh openings is about two millimeters or less. In yet another embodiment, the size of the mesh openings is about 0.1 millimeter.

In one embodiment, the material from which the mesh of the sheet 60 is made includes an absorbable/resorbable material. Examples of resorbable materials include L-lactide and Co DL-lactide materials, cellulose, fibrin, collagen, etc. In another embodiment, a tyrosine-based resorbable polymer, available from TYRX, Inc., Monmouth Junction, N.J., can be employed for the mesh. Other biocompatible materials can also be acceptably used.

As seen in FIG. 3B, the mesh sheet 60 is configured to attach to the port 20 and is configured for placement in a subcutaneous tissue pocket in order to secure the port within the pocket, as will be seen. In the present embodiment, a suitable and biocompatible adhesive can be used to affix the mesh sheet 60 to the bottom surface 22A of the port 20, including those adhesive referenced above in connection with the discussion of FIG. 2. In another embodiment other suitable modes of affixation can be employed including mechanical fixation (via hooks, snaps, ties, etc.), adhesion via vulcanized silicone, heat staking, ultrasonic welding, etc. In yet another embodiment, the mesh sheet can be sewn or otherwise secured about the port.

Figure 4:
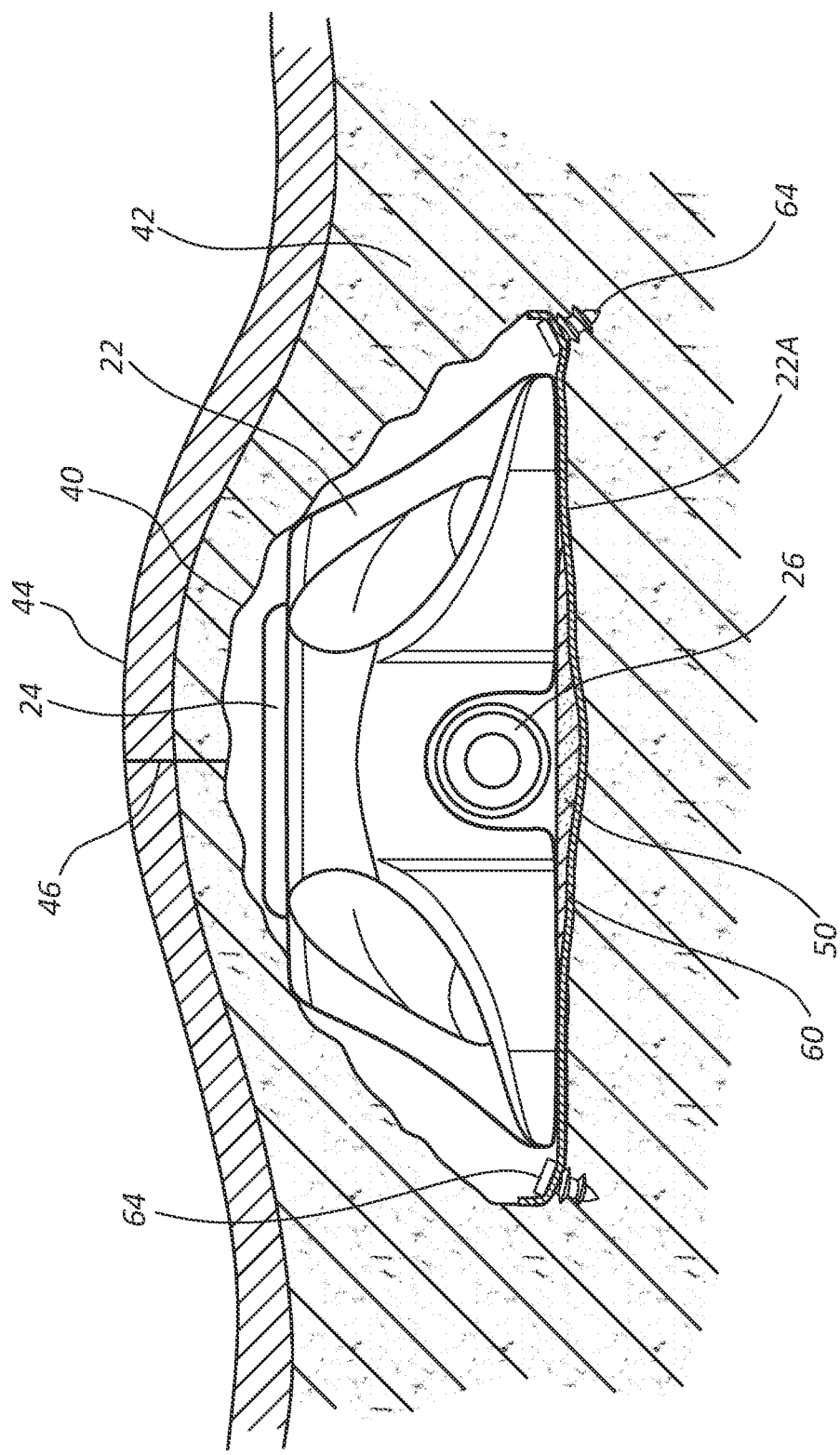
FIG. 4 shows the implantable access port and fixation component of FIG. 3B secured within a tissue pocket according to one embodiment.

FIG. 4 shows the manner in which the mesh sheet 60 is employed as a fixation component to secure the port 20 within the pocket 40. As shown, the port 20—with the mesh sheet 60 attached to the port body bottom surface 22A via the adhesive 50—is disposed within the tissue pocket 40. The mesh sheet 60 in turn is secured to surrounding tissue of the pocket 40 via a plurality of fasteners, in this case threaded, screw-type fasteners 64. As shown, the fasteners 64 extend through the mesh sheet 60 and into the pocket tissue so as to secure the mesh sheet within the pocket, which in turn secures the port 20 in place within the pocket. As before, securement of the port 20 within the pocket 40 prevents undesired port movement, including flipping of the port within the pocket.

It is appreciated that the mesh sheet can be secured to tissue within the pocket by other modes, including adhesives (such as those discussed above in connection with FIG. 2 and including absorbable/resorbable adhesives), wire sutures, traditional sutures, etc.

In one embodiment, the mesh structure of the sheet 60 is employed as a "scaffold" to facilitate tissue in-growth into the sheet and further secure the medical device to the patient's tissue. In the case that it is absorbable/resorbable, the mesh sheet 60 need not be removed when the port 20 is removed from the patient after treatment is complete. In such a case, the fasteners 64 or other fixation component used to secure the mesh sheet 60 in place can be employed as temporary fixation components until tissue in-growth occurs and can be absorbable/resorbable in one embodiment.

It is appreciated that in other embodiments the sheet can be configured as a substantially solid structure (woven or unwoven). It is further appreciated that in one embodiment the mesh sheet includes an antimicrobial substance to reduce or prevent microbial infection of the access port or other implantable device. In one embodiment the antimicrobial substance can include a dual component mixture of Minocycline and Rifampin, available from TYRX, Inc. In another embodiment, a coating including silver and/or iodine can be employed. These and other antimicrobial treatments are therefore contemplated.

Figure 5A:
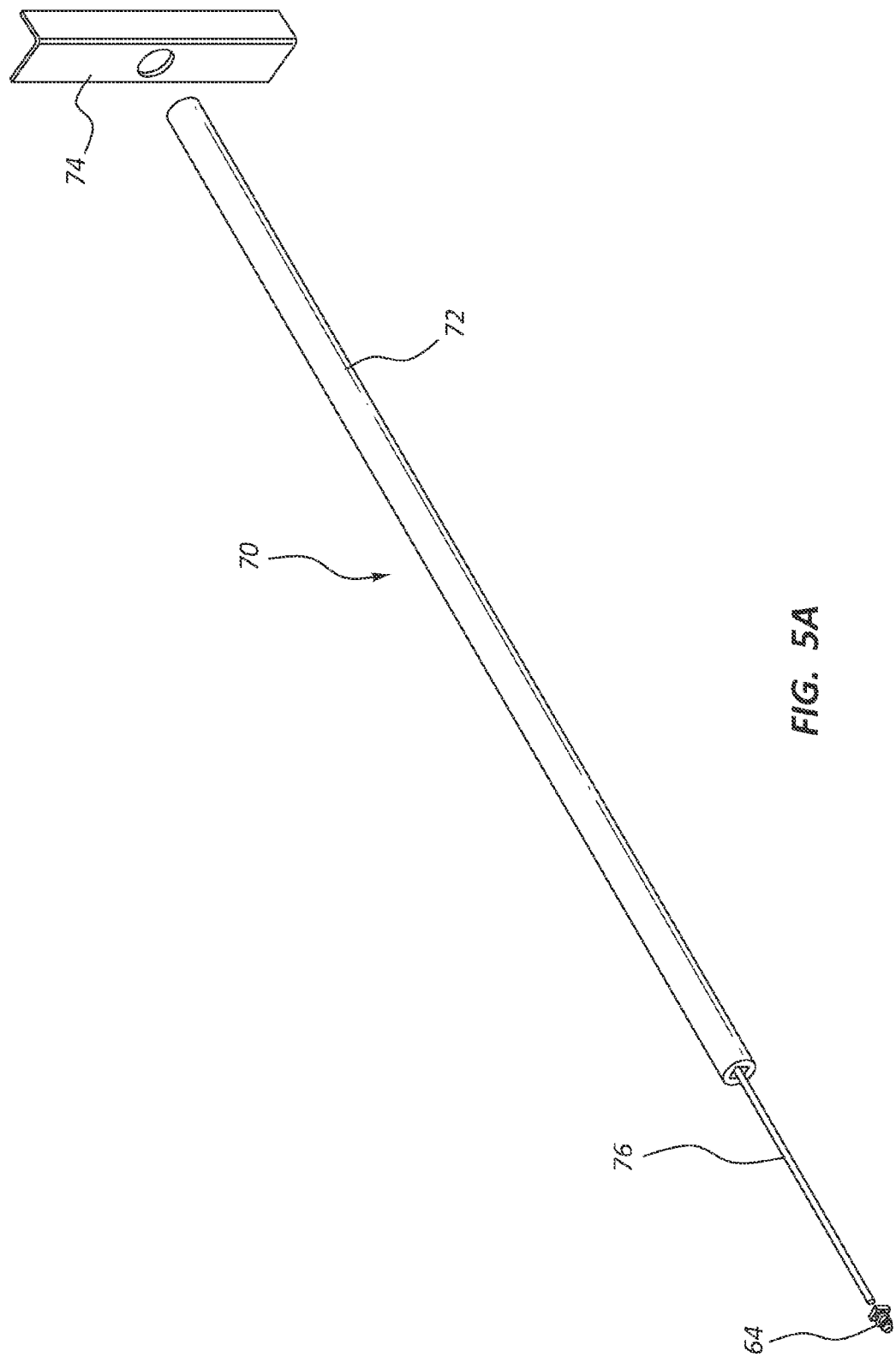
FIGS. 5A and 5B are partially exploded and assembled views, respectively, of an insertion tool for inserting the suture screws shown in FIG. 4 according to one embodiment.
Figure 5B:
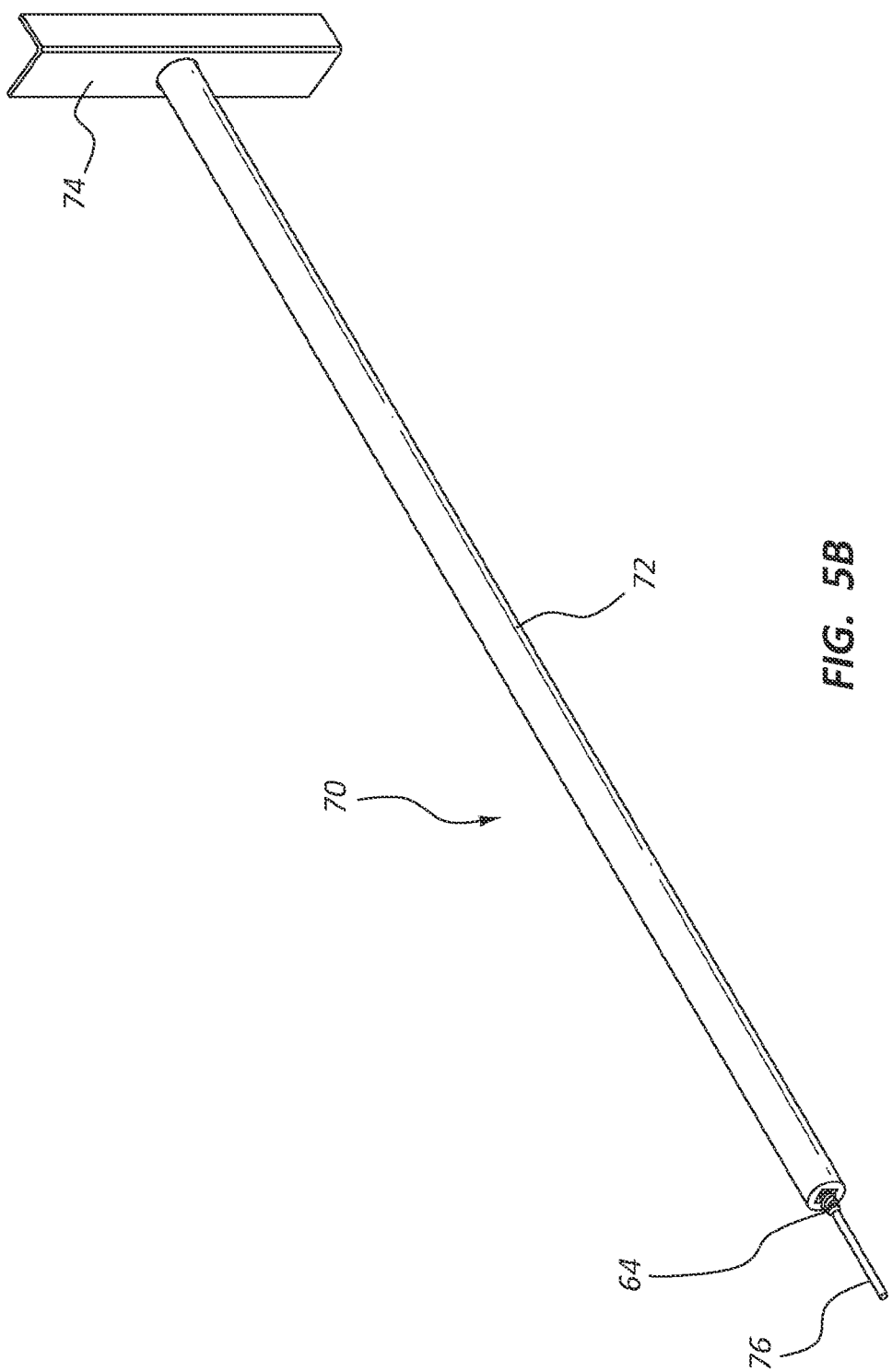

FIGS. 5A and 5B depict various details regarding a suture insertion tool 70 that can be used to insert the fasteners 64 through the mesh sheet 60 and into the tissue of the pocket 40 to secure the port 20 therein (FIG. 4). Again, the fasteners are but one example of fixation components and it is appreciated that the particular design of the insertion tool described here can vary according to the configuration of the fasteners or other fixation component. In one embodiment, for instance, the fasteners include PERMAFIX™ fasteners from Davol Inc, Warwick, R.I. In other embodiments, the fasteners can include, barbed, rivet-like, or other suitable fastener types.

As shown in FIGS. 5A and 5B, the insertion tool 70 includes a round shaft 72 with a handle 74 disposed at a proximal end thereof. A pin guide 76 extends from the distal end of the shaft 72. A plurality of fasteners 64 can be housed within the hollow shaft 72 and can be guided into place within the pocket 40 by the pin guide 76. The square distal end opening of the square shaft 72 can be used as a rotatable driver to thread the each fastener through the mesh sheet 60 and into the tissue, as shown in FIG. 4. It is appreciated that the shape of the insertion tool shaft can vary according to the configuration of the fastener.

Figure 6:
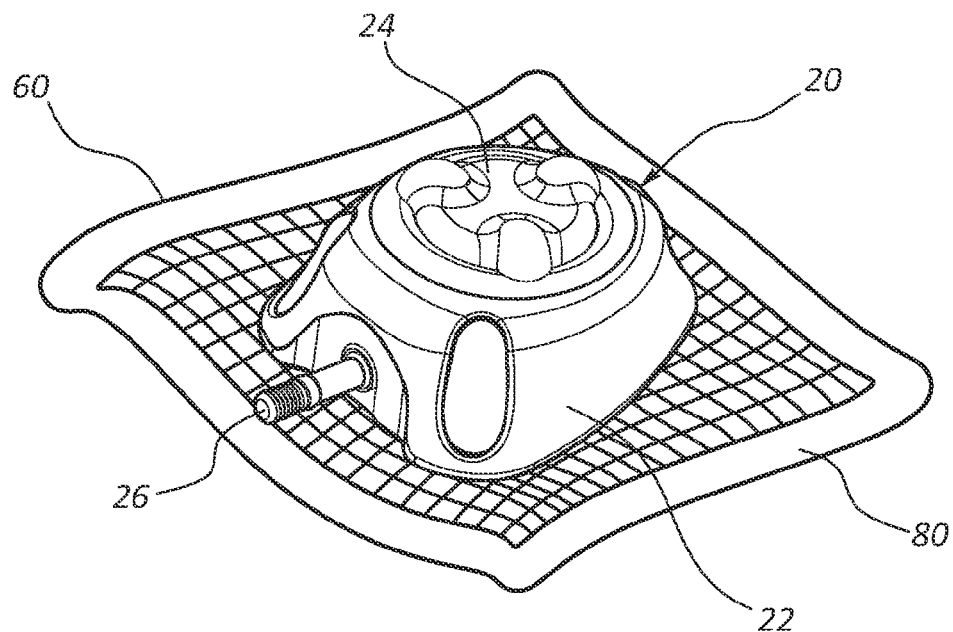
FIG. 6 is a perspective view of a fixation component attached to an implantable access port according to one embodiment.
Figure 7:
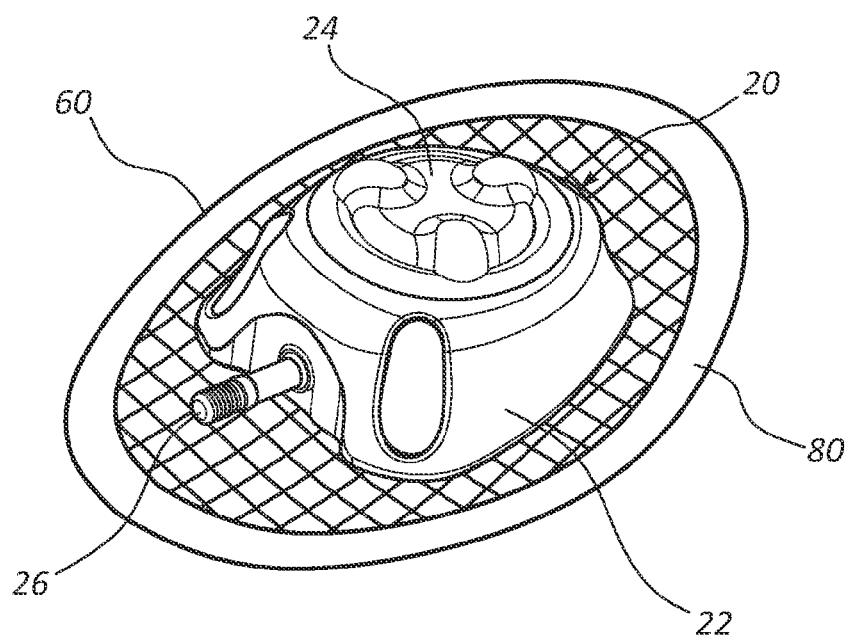
FIG. 7 is a perspective view of a fixation component attached to an implantable access port according to one embodiment.
Figure 8:
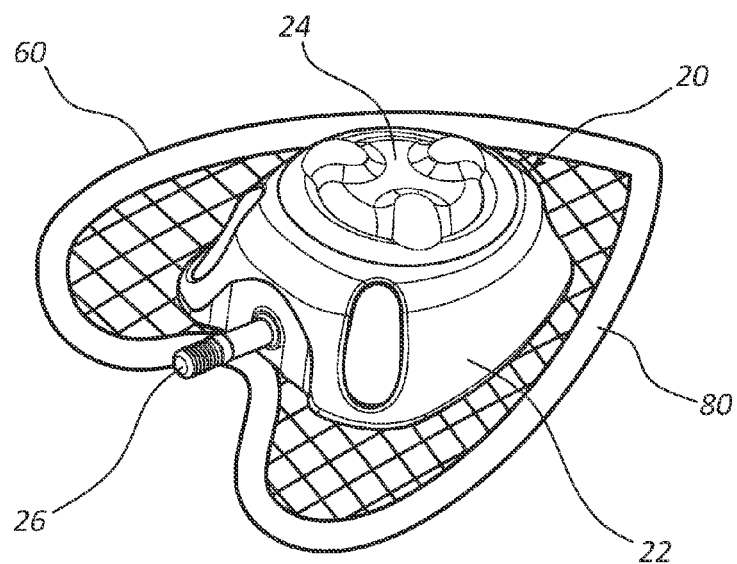
FIG. 8 is a perspective view of a fixation component attached to an implantable access port according to one embodiment.

FIGS. 6, 7, and 8 depict possible shape and edge configurations for the mesh sheet 60. As shown, a substantially solid edge portion 80 is included about the perimeter of each mesh sheet 80. The edge portion 80 serves as a suitable location through which the threaded fasteners 64 (FIG. 4) or other type of fasteners can pierce the sheet 60, thus offering a secure engagement between the fastener and the sheet. The edge portion 80 can also assist in providing a gripping surface for removal of the port from the pocket. Further, the edge portion 80 can assist in preventing unintended pullout of the fasteners inserted through the mesh of the mesh sheet 60. Also, the edge portion 80 provides a smooth perimeter surface for the mesh sheet 60, thus preventing irritation within the pocket 40.

More generally, note that rings, ridges, bands, and other structures can be added to the mesh sheet or other suitable fixation device to enhance connection of the fasteners therewith and/or to facilitate insertion/removal of the medical device from the pocket. These structures can include absorbable/resorbable materials, in one embodiment. Also, the mesh sheet or other fixation component can be manufactured in a variety of sizes, shapes, thicknesses, etc., to accommodate differently-sized implantable devices. In one embodiment, the mesh sheet as a fixation component can fully envelop the medical device and can include a closure device to prevent escape of the medical device therefrom. Again, in one embodiment the mesh sheet can include antimicrobial properties in addition to fixation properties.

Figure 9:
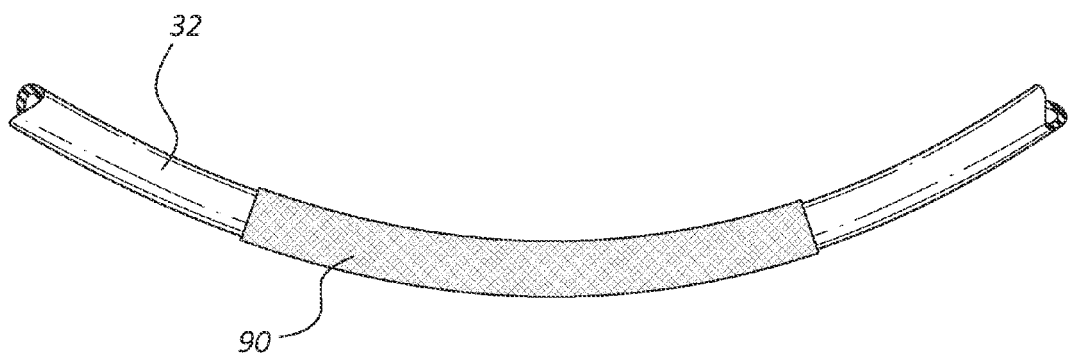
FIG. 9 is a perspective view of a catheter tube including a protective sleeve according to one embodiment.

Reference is made to FIG. 9 in describing details of a hollow, cylindrical protective sleeve 90 that is disposed over a portion of the outer surface of a catheter tube such as the catheter tube 32 of the catheter 30 disposed in the vessel 12, shown in FIG. 1. In the present embodiment, the sleeve 90 defines a fine mesh structure. Desired characteristics of the material from which the mesh of the sleeve 90 is made includes, according to one embodiment, high tensile strength and fine, filamentary structure to enable the formation of the fine mesh configuration of the sleeve. Possible biocompatible materials from which the sleeve can be manufactured include polypropylene, and para-aramid synthetic fiber sold under the trademark KEVLAR®, in one embodiment, though other suitable materials can also be employed, such as those discussed above in connection with the mesh sheet 60 of FIGS. 3A and 3B. In one embodiment, the diameter of the strand material from which the mesh sleeve 90 is formed is about 0.005 inch or less to provide flexibility. In one embodiment, the size of the mesh openings is about two millimeters or less. In yet another embodiment, the size of the mesh openings is about 0.1 millimeter.

In one embodiment, the sleeve mesh has a satin-type weave configuration, though other weaves may also be acceptably used. In the present embodiment, the filamentary material from which the sleeve is made includes a diameter of about 0.001 inch or less, though it is appreciated that a variety of material diameters may acceptably be used.

The sleeve 90 can be placed at any point along the longitudinal length of the catheter tube 32, such as the position shown in FIG. 9, and is affixed to the outer catheter tube surface via a suitable adhesive or other mode for fixation. In another embodiment, the sleeve can be initially slidable along the length of the catheter tube for subsequent fixation once the desired sleeve position is known. In yet another embodiment, the sleeve remains slidable with respect to the catheter tube after final placement of the catheter.

Figure 10:
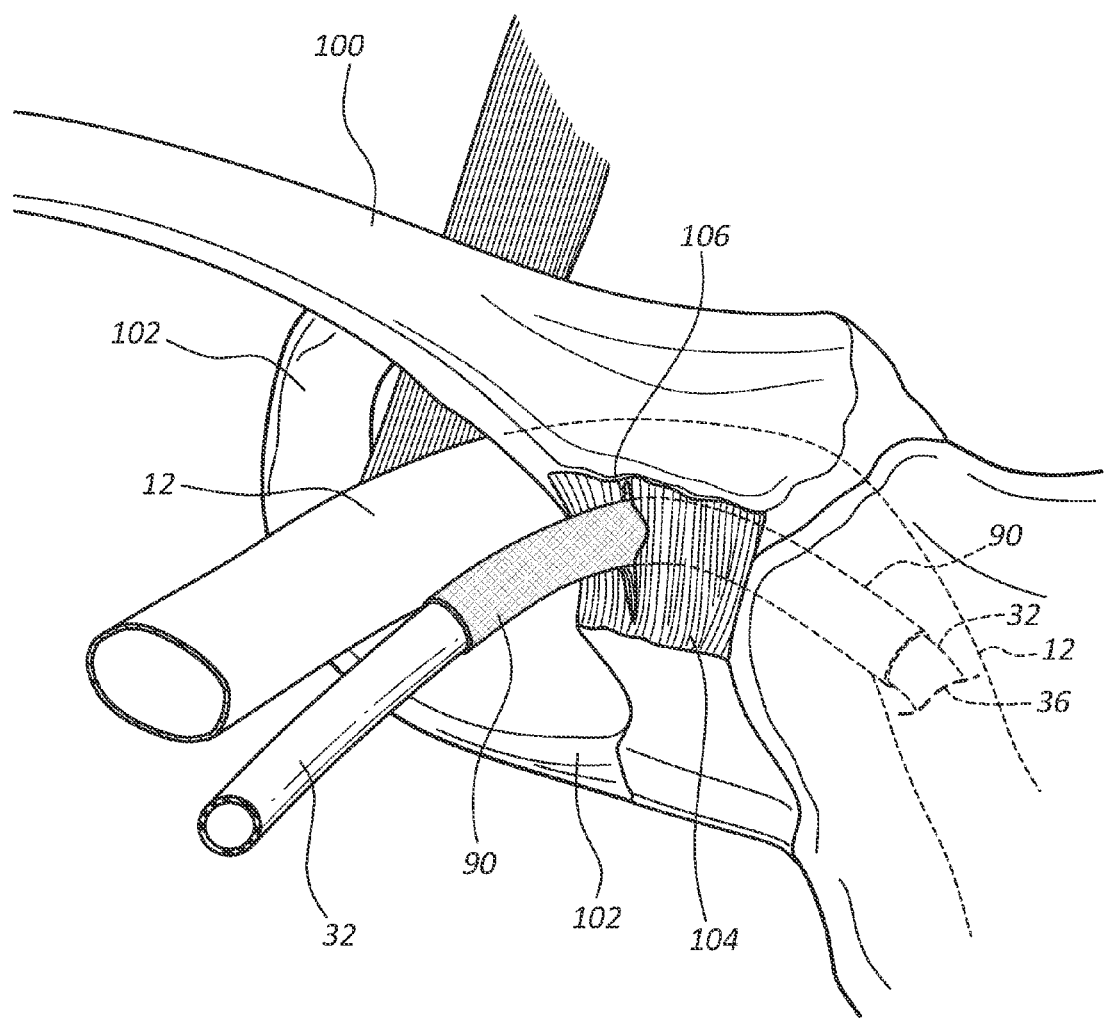
FIG. 10 shows the catheter tube of FIG. 9 in place within the body of a patient according to one embodiment.

In accordance with one embodiment, one possible position for the sleeve 90 along the length of the catheter tube 32 is proximate a point where the catheter tube passes near or through an obstruction that may expose the catheter tube to unintended compression, also referred to herein as pinch-off. FIG. 10 shows one possible pinch-off location. Indeed, FIG. 10 shows a clavicle 100 and a first rib 102 of the patient, between which the subclavian vein 12 passes. The costaclavicular ligament 104 spans between the clavicle 100 and the first rib 102 so as to be positioned proximate the subclavian vein 12. In some cases where it is not inserted into the subclavian vein 12 prior to the vein's passage beneath the clavicle 100, the catheter tube 32 will be advanced by the health care professional such that the catheter tube pierces a hole 106 in and passes through the ligament 104. When this occurs, compressive forces are imposed on the catheter tube 32 by the ligament 104, which may undesirably result in pinch-off.

The sleeve 90 positioned as shown in FIG. 10 is configured to prevent this and other pinch-off scenarios by distributing the compressive load incident on the catheter tube 32 away from the point of tube passage through the ligament 104 and thus cushioning the catheter tube. This results in the lumen(s) defined by the catheter tube remaining patent and functional. Note that this is but one example of a pinch-off scenario where the sleeve can improve catheter tube patency; other positions and configurations are also contemplated. Note further that the sleeve 90 assists in preventing kinking of the catheter tube 32, in one embodiment, and can increase catheter longevity by reducing catheter tube fatigue.

In one embodiment, a tissue growth enhancer can be applied to or otherwise included with the sleeve so as to enhance repair and healing of tissue surrounding the subcutaneous tunnel through which the catheter tube is passed, such as the tunneled portion shown at 34 in FIG. 1. In another embodiment, the sleeve can be treated so as to provide antimicrobial properties. In yet another embodiment, the sleeve can be configured as absorbable/resorbable so as to obviate the need for removal of the sleeve from the tunneled portion of the patient's body when the catheter is no longer needed.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A catheter assembly, comprising:
    an elongate catheter tube defining at least one lumen; and
    a protective mesh sleeve disposed about an external portion of the catheter tube so as to cover at least a portion of a longitudinal length of the catheter tube, the protective mesh sleeve configured to distribute a compressive load on the catheter tube so as to ensure patency of the at least one lumen of the catheter tube.

2. The catheter assembly as defined in claim 1, wherein the mesh sleeve is at least initially slidable along the catheter tube.

3. The catheter assembly as defined in claim 1, wherein the mesh sleeve is affixed to the catheter tube at a location where potential pinch-off of the catheter tube is likely to occur.

4. The catheter assembly as defined in claim 1, wherein the catheter tube is operably connected to an implantable access port and wherein the mesh sleeve is positioned so as to cover a portion of the catheter tube that passes proximate to or penetrates a ligament proximate the clavicle of a patient.

5. The catheter assembly as defined in claim 1, wherein the mesh sleeve includes a satin-type weave configuration.

6. The catheter assembly as defined in claim 1, wherein a material from which the mesh sleeve is formed includes at least one of polypropylene and para-aramid synthetic fiber.

7. The catheter assembly as defined in claim 1, wherein the mesh sleeve is positioned to coincide with a portion of the catheter tube that is positioned in a subcutaneous tunnel extending from a tissue pocket in which a medical device is disposed and a vessel insertion site.

8. The catheter assembly as defined in claim 1, wherein the mesh sleeve includes a tissue growth enhancer.

9. The catheter assembly as defined in claim 1, wherein the mesh sleeve includes an antimicrobial substance to inhibit the presence of microbes on the mesh sleeve.

* * * * *